(12) United States Patent
Couvaras

(10) Patent No.: US 9,339,542 B2
(45) Date of Patent: May 17, 2016

(54) HYPERTENSION REDUCING COMPOSITION

(71) Applicant: John L Couvaras, Scottsdale, AZ (US)

(72) Inventor: John L Couvaras, Scottsdale, AZ (US)

( * ) Notice: Subject to any disclaimer, the term of this patent is extended or adjusted under 35 U.S.C. 154(b) by 0 days.

(21) Appl. No.: 14/252,168

(22) Filed: Apr. 14, 2014

(65) Prior Publication Data

US 2014/0309305 A1 Oct. 16, 2014

Related U.S. Application Data

(60) Provisional application No. 61/812,415, filed on Apr. 16, 2013.

(51) Int. Cl.
| | |
|---|---|
| *A61K 31/195* | (2006.01) |
| *A61K 31/397* | (2006.01) |
| *A61K 31/41* | (2006.01) |
| *A61K 45/06* | (2006.01) |
| *A61K 31/42* | (2006.01) |
| *A61K 31/197* | (2006.01) |
| *A61K 31/165* | (2006.01) |

(52) U.S. Cl.
CPC ............... *A61K 45/06* (2013.01); *A61K 31/42* (2013.01); *A61K 31/165* (2013.01); *A61K 31/195* (2013.01); *A61K 31/197* (2013.01)

(58) Field of Classification Search
CPC .. A61K 31/165; A61K 31/197; A61K 31/195
USPC .................................. 514/563, 210.17, 381
See application file for complete search history.

(56) References Cited

U.S. PATENT DOCUMENTS

| | | | | |
|---|---|---|---|---|
| 4,046,889 | A | * | 9/1977 | Ondetti et al. ........... 514/210.17 |
| 5,196,444 | A | * | 3/1993 | Naka et al. ..................... 514/381 |
| 2005/0182049 | A1 | * | 8/2005 | Howard, Jr. ................ 514/227.5 |

* cited by examiner

*Primary Examiner* — Kevin E Weddington
(74) *Attorney, Agent, or Firm* — Robert A. Parsons; Michael W. Goltry; Parsons & Goltry

(57) ABSTRACT

A composition effective to relax smooth muscles in an individual in an altered state is described. The composition includes a dosage of GABA or GABA-a analog, and a dosage of at least one of an ACE inhibitor and an ARB combined with the dosage of GABA or GABA-a analog into a deliverable form.

10 Claims, No Drawings

HYPERTENSION REDUCING COMPOSITION

CROSS-REFERENCE TO RELATED APPLICATION

This application claims the benefit of U.S. Provisional Patent Application No. 61/812,415, filed 16 Apr. 2013.

FIELD OF THE INVENTION

This invention relates to hypertension medications.

More particularly, the present invention relates to substances which relax smooth muscle tissue.

BACKGROUND OF THE INVENTION

Hypertension in humans is a condition wherein the blood pressure is elevated. This can be due to various causes, such as constriction of the blood vessels. Angiotensin II is a potent vasoconstrictor in the human body. It is part of the Renin-Angiotensin system and is activated to increase blood pressure via constriction of the vessels. Angiotensin II is formed from angiotensin I in the blood by an angiotensin converting enzyme (ACE). ACE inhibitors are substances that slow (inhibit) the activity of the enzyme, which decreases the production of angiotensin II. As a result, the blood vessels are less constricted and blood pressure is reduced.

Another substance used for reducing blood pressure is Angiotensin receptor blockers (ARBs). Angiotensin II receptor blockers (ARBs) are substances that block the action of angiotensin II by preventing angiotensin II from binding to angiotensin II receptors on blood vessels. As a result, the blood vessels are less constricted and blood pressure is reduced.

Preventing the formation of angiotensin II by an angiotensin converting enzyme inhibitor or blocking the action of angiotensin II on the AT1 constricting receptor has been well documented and patented in various doses and drugs, namely Angiotensin Converting Enzyme Inhibitors (ACE inhibitors) and Angiotensin Receptor Blockers (ARBs). While these substances have been shown to work, they also have side effects which are not desirable, and would be better if used in smaller doses. However, reducing the dosage also reduces the effectiveness of the substance.

It would be highly advantageous, therefore, to remedy the foregoing and other deficiencies inherent in the prior art.

An object of the present invention is to provide a composition which synergistically relaxes smooth muscle.

Another object of the present invention is to provide a composition increasing the effectiveness of Angiotensin Converting Enzyme Inhibitors (ACE inhibitors) and Angiotensin Receptor Blockers (ARBs).

SUMMARY OF THE INVENTION

Briefly, to achieve the desired objects and advantages of the instant invention provided is a composition effective to relax smooth muscles in an individual in an altered state. The composition includes a dosage of GABA or GABA-a analogue, and a dosage of at least one of an ACE inhibitor and a ARB combined with the dosage of GABA or GABA-a analogue into a deliverable form.

In cooperation with at least one of an ACE-I having a relative dosage effective to reduce blood pressure a determined amount and an ARB having a relative dosage effective to reduce blood pressure a determined amount, a composition is provided. The composition includes a dosage of GABA or GABA-a analogue and a dosage of at least one of an ACE inhibitor and an ARB, combined with the dosage of GABA or GABA-a analogue into a deliverable form. In the presence of GABA or GABA-a analogue the dosage of at least one of the ACE inhibitor is smaller than the relative dosage to supply the dosage effective to reduce blood pressure by the determined amount and the ARB is smaller than the relative dosage to supply the dosage effective to reduce blood pressure the determined amount.

Also provided is a method of relaxing smooth muscles in an individual having GABA receptors expressed in the individual's smooth muscles and endothelium. The method includes the steps of providing a composition of a dosage of GABA or GABA-a analogue and a dosage of at least one of an ACE inhibitor and a ARB combined into a deliverable form. The composition is delivered to an individual's circulatory system. The level of angiotensin II in the individual is reduced through the action of the dosage of at least one of the ACE inhibitor and/or the ARB during a period of time. The GABA receptors are activated through the action of the GABA or GABA-a analog during the period of time to promote production and release of smooth muscle relaxing substances by the activation of the GABA-a receptors.

DETAILED DESCRIPTION OF A PREFERRED EMBODIMENT

The present invention is a combination of an existing class of anti-hypertensive drugs, Angiotensin Converting Enzyme Inhibitors (ACE-I) and/or Angiotensin Receptor Blockers (ARBs), with the amino acid GABA or GABA-a analog, to improve the smooth muscle relaxation response, improved vasodilation and improved blood pressure reducing response, or reducing the dose of current ACE inhibitor and/or ARBs with GABA or GABA-a analogue and achieve the same response. GABA-a analogue is being used as a term to define a compound that has a potential to bind to a GABA-a receptor and stimulate a response. An example of a GABA-a agonist is Muscimol and the like. Thus, the intent is to create a new class of drugs composed of compounds from either ACE-I or ARBs or combination thereof, with an effective dose of GABA or GABA-a agonist/analogue to stimulate the release of vasodilator compounds such as prostaglandin $I_2$ also referred to as prostacyclin (PGI2) to reduce blood pressure or other effects from the relaxation of smooth muscles. This provides an improvement in blood pressure with a lesser amount of ACE-I, ARBs, or combinations thereof, thus having less side effects and/or toxicity. Conversely, the composition will enhance the effectiveness of the existing ACE-I and ARBs Angiotensin-converting enzyme (ACE) inhibitors block the angiotensin converting enzyme which is needed to form a substance that narrows blood vessels. As a result, blood vessels relax and widen (dilate), making it easier for blood to flow through the vessels, which reduces blood pressure. These medicines also increase the release of water and sodium to the urine, which also lowers blood pressure.

Angiotensin II receptor, type 1 or $AT_1$ receptor is an angiotensin receptor and mediates the cardiovascular effects of angiotensin II, for our purposes vasoconstriction effects, and is an important effector controlling blood pressure and volume in the cardiovascular system. ARBs are Angiotensin II, type 1 ($AT_1$) receptor antagonists. That is, they block the activation of angiotensin II $AT_1$ receptors. Blockage of $AT_1$ receptors prevents vasoconstriction, reduces secretion of vasopressin, and reduces production and secretion of aldosterone, amongst other actions. The combined effect reduces blood pressure.

During experimentation between uterine vessels and systemic vessels during pregnancy (altered state), an inverse response between uterine and systemic vessels and their ability to secrete prostacyclin (PGI2), a short acting smooth muscle relaxer, has been found. Systemic vessels exposed to GABA, in the presence of Angiotensin Converting Enzyme inhibitors (ACE inhibitor) will prevent vasoconstriction due to an increased PGI2. Uterine vessels require GABA and angiotensin II to increase PGI2 and dilate. This mechanism appears to be feto-protective in cases of hemorrhage and low blood volume. During these times angiotensin II will increase, dilating the uterine circuit and constricting the systemic circuit, thereby allowing the maternal blood to pass by the baby, prolonging the baby's chances of survival. It is believed that this mechanism is present in every human but disappears shortly after birth, then reappears in later adult altered cardiovascular states. Altered cardiovascular states include essential hypertension, pregnancy, pulmonary hypertension, Alzheimer's disease, inflammatory bowel disease, anesthesia, and the like. Thus, the composition of the present invention is useful for relaxing smooth muscle and improving blood flow when in the altered state.

The inventor has found that the blood vessels, smooth muscle and endothelium of an individual express GABA-a receptors during an "altered state" of the individual. The term altered state is intended to mean a state in which the person is outside the norm, having conditions such as essential hypertension, pulmonary hypertension, malignant hypertension, inflammation, metabolic dysfunction, pregnancy, preeclampsia, under general anesthesia, infection and/or sepsis, autoimmune diseases, renal failure, and the like. GABA-a receptors release and/or produce vasodilatory substances and smooth muscle relaxers in the presence of GABA or GABA-a analogs, but only in the presence of AII inhibition or blockade. The presence of angiotensin II inhibits the functioning of these expressed GABA-a receptors, preventing the release of these substances. In other words, the angiotensin II acts to suppress the action of the GABA-a receptors. By administering ACE inhibitors or ARBs, the angiotensin II present in the system is reduced, and in the presence of GABA or GABA-a analog to bind to the GABA-a receptors, results in the release and/or production of the vasodilator substances and smooth muscle relaxers. GABA or GABA-a analog binding to the GABA-a receptors induces release and/or production, for example, of $PGI_2$. GABA alone and ACE inhibitors or ARBs alone do not have the same effect, as the GABA is ineffective with GABA-a receptors inhibited, and ACE inhibitors and ARBs do not stimulate the GABA-a receptors in the production/release of $PGI_2$. Together, a synergistic effect occurs which greatly increases the effectiveness of each of the substances used, over what would occur when used singly. Thus, a dosage of ACE inhibitor and/or ARB which reduces blood pressure a determined amount, can be reduced to a smaller dosage with the addition of GABA or GABA-a analog.

The preferred composition can be administered in various dosages, such as GABA doses of 1 mg/day to 10 gms/day and in various ACE-I doses of 1 mg/day to 450 mgs/day, or in various ARB doses of 1 mg/day to 1000 mg/day. Dosage can also include any combination of GABA doses 1 mg/day to 10 gms/day and combination of ACE-I and ARBs. The new drug will be oral or IV, and dosed once, twice or thrice daily.

Ace inhibitors and ARBs tend to have a relatively long half-life in an individual's system. GABA has a relatively short half-life. In a preferred embodiment, the composition is provided in a time release form, with the GABA being released over a longer period of time. For example, a tablet can be provided which includes a dosage of ACE inhibitor and/or ARBs in an outer layer, and inner layers of GABA which release over a period of time. In this manner, the ACE inhibitor and/or ARBs are delivered into the system and remain there for a period of time. The GABA, having a shorter time in an individual's system, is released over that period of time to provide a constant source of GABA to interact with the ACE inhibitor and/or ARBs. It will be understood by one skilled in the art that various mechanisms for releasing GABA over a period of time that ACE inhibitors and ARBs are present in the system can be employed, such as capsules, tablets and the like.

While the present invention has been described primarily in terms of reducing blood pressure, it will be understood that since the GABA-a receptors were found to be present in substantially any smooth muscle and endothelium, the composition of the present invention can be used to effect any of the various vascular circuits such as pulmonary, coronary, cutaneous, splanchnic and the like. In effect, the composition of the present invention can be used to relax any smooth muscle to achieve various effects such as increasing blood flow in the skin, relieve inflammatory bowel disease and the like. Likewise, since the main purpose of the composition is to improve blood flow through blood vessels, many issues are potentially resolved using this composition.

Various changes and modifications to the embodiments herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

The invention claimed is:

1. A composition effective to relax smooth muscles in an individual in an altered state, the composition comprising:
    a dosage of GABA or GABA-a analogue; and
    a dosage of at least one of an ACE inhibitor and a ARB combined with the dosage of GABA or GABA-a analogue into a deliverable form.

2. A composition as claimed in claim 1 wherein the deliverable form includes one of tablets, capsules and IVs.

3. A composition as claimed in claim 1 wherein the deliverable form is a tablet including the GABA or GABA-a analog in time release form.

4. A composition as claimed in claim 1 wherein the deliverable form is a capsule including the GABA or GABA-a analog in time release form.

5. A composition as claimed in claim 1 wherein the GABA or GABA-a analog dose is in the range of 1 mg/day to 10 gms/day, and at least one of the ACE-I dose being in the range of 1 mg/day to 450 mgs/day and the ARB dose being in the range of 1 mg/day to 1000 mg/day.

6. In cooperation with at least one of an Ace-I having a relative dosage effective to reduce blood pressure a determined amount and an ARB having a relative dosage effective to reduce blood pressure a determined amount, a composition comprising:
    a dosage of GABA or GABA-a analogue;
    a dosage of at least one of an ACE inhibitor and an ARB, combined with the dosage of GABA or GABA-a analogue into a deliverable form; and
    in the presence of GABA or GABA-a analogue the dosage of at least one of the ACE inhibitor is smaller than the relative dosage to supply the dosage effective to reduce blood pressure the determined amount and the ARB is smaller than the relative dosage to supply the dosage effective to reduce blood pressure the determined amount.

7. A composition as claimed in claim 6 wherein the deliverable form includes one of tablets, capsules and IVs.

8. A composition as claimed in claim 6 wherein the deliverable form is a tablet including the GABA or GABA-a analog in time release form.

9. A composition as claimed in claim 6 wherein the deliverable form is a capsule including the GABA or GABA-a analog in time release form.

10. A composition as claimed in claim 6 wherein the GABA or GABA-a analog dose is in the range of 1 mg/day to 10 gms/day, and at least one of the ACE-I dose being in the range of 1 mg/day to 450 mgs/day and the ARB dose being in the range of 1 mg/day to 1000 mg/day.

\* \* \* \* \*